United States Patent [19]

Chambers

[11] Patent Number: 4,646,727

[45] Date of Patent: Mar. 3, 1987

[54] LEG CAST COVER

[76] Inventor: David H. Chambers, 2890 Griffin Rd., Suite #4, Fort Lauderdale, Fla. 33004

[21] Appl. No.: 755,707

[22] Filed: Jul. 16, 1985

[51] Int. Cl.[4] ............................................. A61F 13/00
[52] U.S. Cl. .................................... 128/82; 128/153; 36/7.1 R
[58] Field of Search ................. 128/82, 153, 165, 166, 128/166.5; 2/22, 61, 239, 240; 36/7.1 R

[56] References Cited

U.S. PATENT DOCUMENTS

| | | | |
|---|---|---|---|
| 1,330,315 | 2/1920 | Hagan | 2/239 |
| 2,596,211 | 5/1952 | Comfort | 128/165 X |
| 3,416,518 | 12/1968 | Samuels et al. | 128/165 X |
| 3,487,830 | 1/1970 | Pruett | 2/239 X |
| 3,735,759 | 5/1973 | Mackay | 128/165 X |
| 4,494,536 | 1/1985 | Latenser | 128/153 |

*Primary Examiner*—Stephen F. Husar
*Attorney, Agent, or Firm*—Seed and Berry

[57] ABSTRACT

A leg cast has a foot sock complemented by a leg sock having a heel portion and a foot opening adjoining the heel portion. A portion of the leg sock, defining the foot opening overlaps the inner end of the foot sock.

8 Claims, 3 Drawing Figures

LEG CAST COVER

DESCRIPTION

1. Technical Field

The present invention relates to covers for leg and ankle casts adapted to cover the foot and cast of the injured person.

2. Disclosure of Invention

The invention aims to provide an improved cast cover which covers the entire foot and cast, is easy to apply, fits various sizes of casts and feet, can be laundered, is relatively easy and inexpensive to make, and has an attractive finished appearance.

In carrying out these objectives it is preferred to use tubular knit fabric material having an elastic character for stretching its girth. From this material there is formed complementing foot and leg covers (socks) which overlap when applied to jointly cover the cast and foot. The foot sock has an elastic ankle strap which retains it on the foot, and the leg sock has a heel portion adjoining a foot opening. The portion of the leg sock surrounding this foot opening overlaps the foot sock. It is preferred to provide elastic bands surrounding the openings in the foot and leg socks.

BEST MODE FOR CARRYING OUT THE INVENTION

Figure 1:
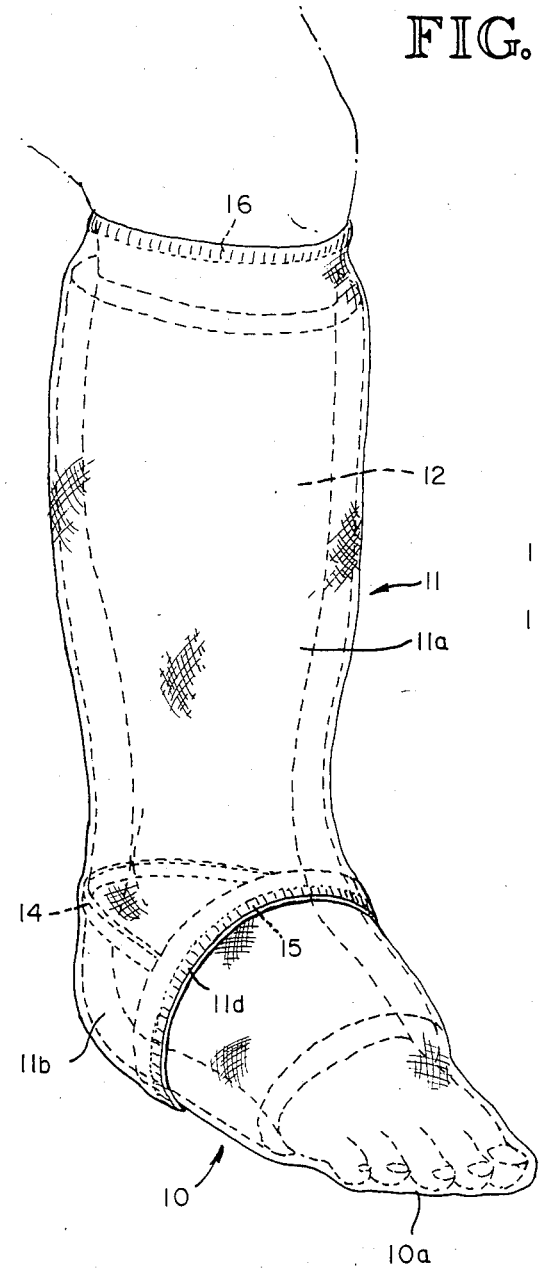
FIG. 1 is a perspective view illustrating the cast cover of the present invention in operative positive on a leg having a leg and ankle cast.
Figure 2:
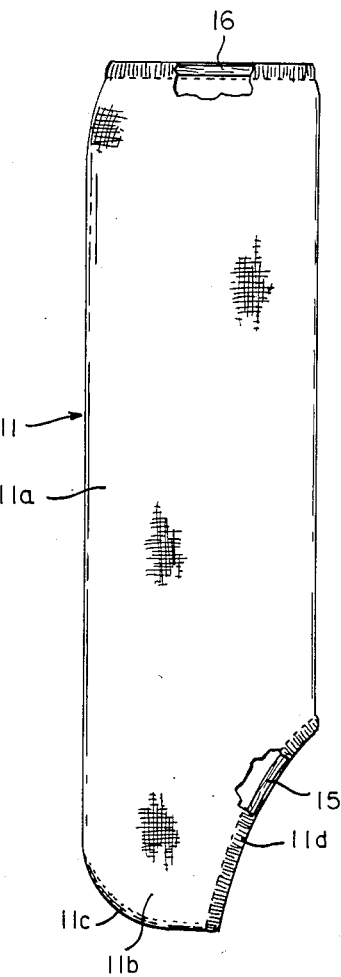
FIG. 2 is a side elevational view of the leg sock component of the cast cover with parts thereof broken away.
Figure 3:
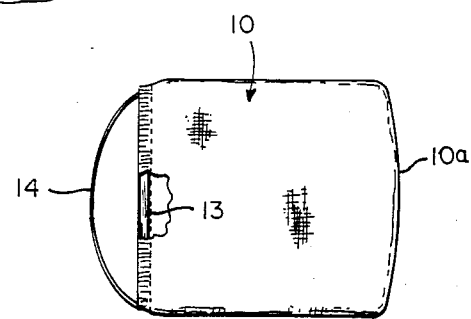
FIG. 3 is a plan view of the foot sock component of the cast cover partly broken away.

Referring to the drawings, it is seen that the cast cover of the present information comprises a foot sock 10 and a leg sock 11 formed to collectively cover the injured person's foot and a leg and ankle cast 12. Both socks 10, 11 are preferably formed from a suitable stretch material such as a tubular knit fabric which will permit the girth of the socks to expand as required to fit over the foot and cast.

The foot sock 10 is in the form of a pocket with a curved closed end 10a, and has the open end portion doubled under around an elastic rim band 13 and stitched to the main body of the sock. An elastic heel strap 14 is anchored at its ends by stitching to the doubled over rim portion of the foot sock at locations opposite the ends of the curved closed end 10a.

The leg sock 11 has a sleeve portion 11a and an integral heel portion 11b with a curved bottom edge defined by a seam 11c. A slightly concave foot entry 11d is provided between the front end of the seam 11c and front of the leg portion 11a. This entry 11d and the open upper end of the leg sock are provided with elastic bands 15, 16 and are finished in the same manner as the rim of the foot sock 10.

When the cast cover is in cast covering position it is preferred to have the ankle band 14 hidden from view by the leg sock 11 in which case the foot entry portion of the leg sock overlaps the foot sock 10. To this end, the foot sock 10 can first be pulled onto the injured person's foot and over the lower end of the cast 12 and then the elastic band 14 is stretched beneath the heel to engage the back of the ankle portion of the cast. Next the leg sock 11 is pulled over the foot sock 10, and then around the heel portion and over the leg portion of the cast. As a result the portion of the leg sock 11 adjacent the foot entry 11d overlaps the foot sock 10 thereby providing a complete attractive cover for the foot and cast.

It will be appreciated that, although specific embodiments of the invention have been described herein for purposes of illustration, various modifications may be made without departing from the spirit and scope of the invention. Accordingly, the invention is not limited except by the appended claims.

I claim:

1. A cast covering comprising:
   a foot sock having a closed toe end and an open end,
   an elastic ankle strap having its ends connected to the foot sock adjacent said open end to form a loop,
   a leg sock having a leg portion open at one end and having a heel portion at the other end, said leg sock having a foot opening adjoining the heel portion, said foot and leg socks being adapted to jointly cover a leg and ankle cast and the foot of the wearer of the cast with the ankle strap looped over the ankle area of the cast and the leg sock overlapping the foot sock.

2. A cast cover according to claim 1 in which the rim portion of the leg sock surrounding said foot opening in the leg sock has an elastic band connected thereto to surround said foot opening.

3. A cast cover according to claim 2 in which the rim portion of the foot sock surrounding said open end thereof also has an elastic band connected thereto to surround said open end.

4. A cast cover according to claim 1 in which the respective rim portions of the leg sock surrounding the open end thereof and the foot opening each have an elastic band connected thereto to surround said open end and foot opening.

5. A cast cover according to claim 4 in which the rim portion of the foot sock surrounding said open end thereof also has an elastic band connected thereto to surround said open end.

6. A cast cover according to claim 1 in which said leg sock is made from tubular knit fabric material which can be stretched to vary the diameter for various cast sizes.

7. A cast cover according to claim 6 in which said foot sock is also made from tubular knit fabric material which can be stretched to vary the diameter.

8. A cast cover comprising,
   a foot sock having a closed toe end and an open end with an elastic rim,
   an elastic heel loop connected to the foot sock adjacent the elastic rim,
   a leg sock having an open upper end with an elastic rim and a heel portion, said leg sock haivng a foot opening adjoining the heel portion and having an elastic rim for overlapping the foot sock when the leg sock covers a leg and ankle cast and the foot sock is fitted over the foot with the heel lock passing round the ankle portion of the cast.

* * * * *